(12) United States Patent
Alford et al.

(10) Patent No.: US 11,612,738 B2
(45) Date of Patent: *Mar. 28, 2023

(54) DEVICES, SYSTEMS AND METHODS TO REDUCE COUPLING OF A CONDUCTOR WITHIN AN IMPLANTABLE MEDICAL LEAD

(71) Applicant: MEDTRONIC, INC., Minneapolis, MN (US)

(72) Inventors: Jamu K. Alford, Ham Lake, MN (US); Spencer Fodness Bondhus, Columbia Heights, MN (US); Michael Kalm, Spring Lake Park, MN (US); James M. Olsen, Plymouth, MN (US); Brian T. Stolz, Bloomington, MN (US); Richard T. Stone, Minneapolis, MN (US); Bryan D. Stem, Minneapolis, MN (US); John D. Welter, Plymouth, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 113 days.

This patent is subject to a terminal disclaimer.

(21) Appl. No.: 16/995,492

(22) Filed: Aug. 17, 2020

(65) Prior Publication Data

US 2020/0376260 A1 Dec. 3, 2020

Related U.S. Application Data

(63) Continuation of application No. 16/005,622, filed on Jun. 11, 2018, now Pat. No. 10,751,525, which is a continuation of application No. 14/568,547, filed on Dec. 12, 2014, now Pat. No. 9,993,638.

(60) Provisional application No. 61/916,171, filed on Dec. 14, 2013.

(51) Int. Cl.
*A61N 1/05* (2006.01)
*A61N 1/08* (2006.01)

(52) U.S. Cl.
CPC .............. *A61N 1/05* (2013.01); *A61N 1/086* (2017.08)

(58) Field of Classification Search
CPC ........................................................ A61N 1/05
USPC ........................................................ 607/113
See application file for complete search history.

(56) References Cited

U.S. PATENT DOCUMENTS

| 2010/0022950 | A1* | 1/2010 | Anderson | A61B 5/05 604/100.01 |
| 2012/0209365 | A1* | 8/2012 | Seifert | A61N 1/05 29/601 |
| 2015/0170792 | A1* | 6/2015 | Alford | A61N 1/05 174/102 R |

* cited by examiner

*Primary Examiner* — Nicole F Lavert
(74) *Attorney, Agent, or Firm* — Withers & Keys, LLC

(57) ABSTRACT

Conductors within an implantable medical lead that carry stimulation signal signals are at least partially embedded within a lead body of the medical lead over at least a portion of the length of the conductors while being surrounded by a radio frequency (RF) shield. A space between the shield and the conductors is filled by the presence of the lead body material such that body fluids that infiltrate the lead over time cannot pool in the space between the shield and the conductors. The dielectric properties of the lead body are retained and the capacitive coupling between the shield and the conductors continues to be inhibited such that current induced on the shield is inhibited from being channeled onto the conductors. Heating at the electrodes of the medical lead is prevented from becoming excessive.

26 Claims, 7 Drawing Sheets

DEVICES, SYSTEMS AND METHODS TO REDUCE COUPLING OF A CONDUCTOR WITHIN AN IMPLANTABLE MEDICAL LEAD

RELATED APPLICATIONS

The present application is a continuation of U.S. patent application Ser. No. 16/005,622, now U.S. Pat. No. 10,751,525, filed on Jun. 11, 2018, which is a continuation of U.S. Pat. No. 9,993,638, filed on Dec. 12, 2014, which claims priority to U.S. Provisional Appl. No. 61/916,171, filed on Dec. 14, 2013.

TECHNICAL FIELD

Embodiments are related to implantable medical leads having shields for blocking electromagnetic energy from coupling onto conductors. More specifically, embodiments are related to reducing the coupling of the shield to the conductor(s) within the implantable medical device.

BACKGROUND

Implantable medical leads are used to provide electrical stimulation from a pulse generator to a target site within a body of a patient. The lead includes electrical conductors that extend from a proximal end that is coupled to the pulse generator to a distal end. The conductors carry stimulation signals to electrodes on the distal end that are positioned at the target site and deliver the stimulation signals to the tissue.

The presence of the lead presents a risk if the patient undergoes a magnetic resonance imaging (MRI) scan. Radio frequency (RF) energy that is present during the MM scan may couple to the conductor(s) within the lead which results in electrical current on the conductor that can cause potentially dangerous heating of tissue nearby the electrode. This is especially problematic for neurostimulation leads where the electrode is placed in very sensitive neurological tissue such as within the brain or spine.

Various techniques have been devised to try to lessen the current being induced onto the conductor by the RF energy to thereby lessen the amount of heating at the electrode. One technique is to include a conductive RF shield that surrounds the conductor. The RF energy is largely blocked from reaching the conductor and the induced current and tissue heating are reduced.

The conductor is typically located in a lumen of the lead while the shield may be present outside of the lumen, typically in a polymer jacket. Over time, body fluids infiltrate the polymer jacket of the lead and reach the lumen which fills with the fluid. Thus, a significant amount of body fluid could be present between the shield and the conductor being shielded. Because the body fluid presents a high dielectric constant, capacitive coupling may occur to some degree between the shield and the conductor which could result in some of the RF energy being transferred to the conductor.

SUMMARY

Embodiments address issues such as these and others by providing a lead where at least a portion of the diameter of the conductor is embedded within a lead body that contains the shield such that a space between a shield and the conductor is entirely filled with the lead body material. This eliminates body fluid from being pooled between the shield and the conductor and thereby lessens the capacitive coupling that occurs to thereby limit increases in heating over time.

Embodiments provide a method of providing a medical lead that includes providing a conductor having a diameter and providing a radio frequency (RF) shield that surrounds the conductor such that a space exists between the shield and the conductor. The method further involves providing a lead body with a lumen where the lead body encapsulates the shield and surrounds the conductor with a portion of the conductor diameter being embedded within the lead body and the lead body filling the space. The method further involves providing an electrode attached to the lead body and electrically coupled to the conductor.

Embodiments provide a method of providing a medical lead. The method involves forming an inner lead body layer of a lead body about a conductor to embed a portion of a diameter of the conductor within the inner lead body layer and positioning a radio frequency (RF) shield about the lead body inner layer. The method further involves forming an outer lead body layer of the lead body about the shield and the inner lead body layer to encapsulate the shield and to bond with the inner lead body layer and providing an electrode attached to the lead body and electrically coupled to the conductor.

Embodiments provide an implantable medical lead that includes a conductor having a diameter and a radio frequency (RF) shield that surrounds the conductor such that a space exists between the shield and the conductor. The lead includes a lead body with a lumen, the lead body encapsulating the shield and surrounding the conductor with a portion of the conductor diameter being embedded within the lead body and the lead body filling the space. The lead further includes an electrode attached to the lead body and electrically coupled to the conductor.

Embodiments provide an implantable medical system that includes a pulse generator and a medical lead. The medical lead includes a conductor having a diameter, the conductor being electrically coupled to the pulse generator. The medical lead includes a radio frequency (RF) shield that surrounds the conductor such that a space exists between the shield and the conductor. The lead includes a lead body with a lumen and the lead body encapsulates the shield and surrounds the conductor with a portion of the conductor diameter being embedded within the lead body and with the lead body filling the space. The lead further includes an electrode attached to the lead body and electrically coupled to the conductor.

Embodiments provide an implantable medical lead that includes a conductor having a diameter and a radio frequency (RF) shield that surrounds the conductor such that a space exists between the shield and the conductor. The lead includes a lead body with a lumen, the lead body encapsulating the shield and surrounding the conductor with a first longitudinal section of the conductor diameter being at least partially embedded within the lead body and with a second longitudinal section of the conductor diameter that is distal of the first section and that is less embedded by the lead body than the first section, and the lead body filling the space between the first longitudinal section of the conductor and the shield. The lead also includes an electrode attached to the lead body and electrically coupled to the conductor.

DETAILED DESCRIPTION

Embodiments provide methods, medical leads, and systems where the medical leads have one or more conductors that are at least partially embedded for at least a portion of the length of the lead and where a shield is present within the lead and surrounds the conductors. Where the conductor is at least partially embedded, the lead body fills the space between the conductor and the shield so that fluids that infiltrate the lead body and reach a lumen of the lead body over time cannot pool between the conductor and the shield where the conductor is at least partially embedded.

Figure 1:
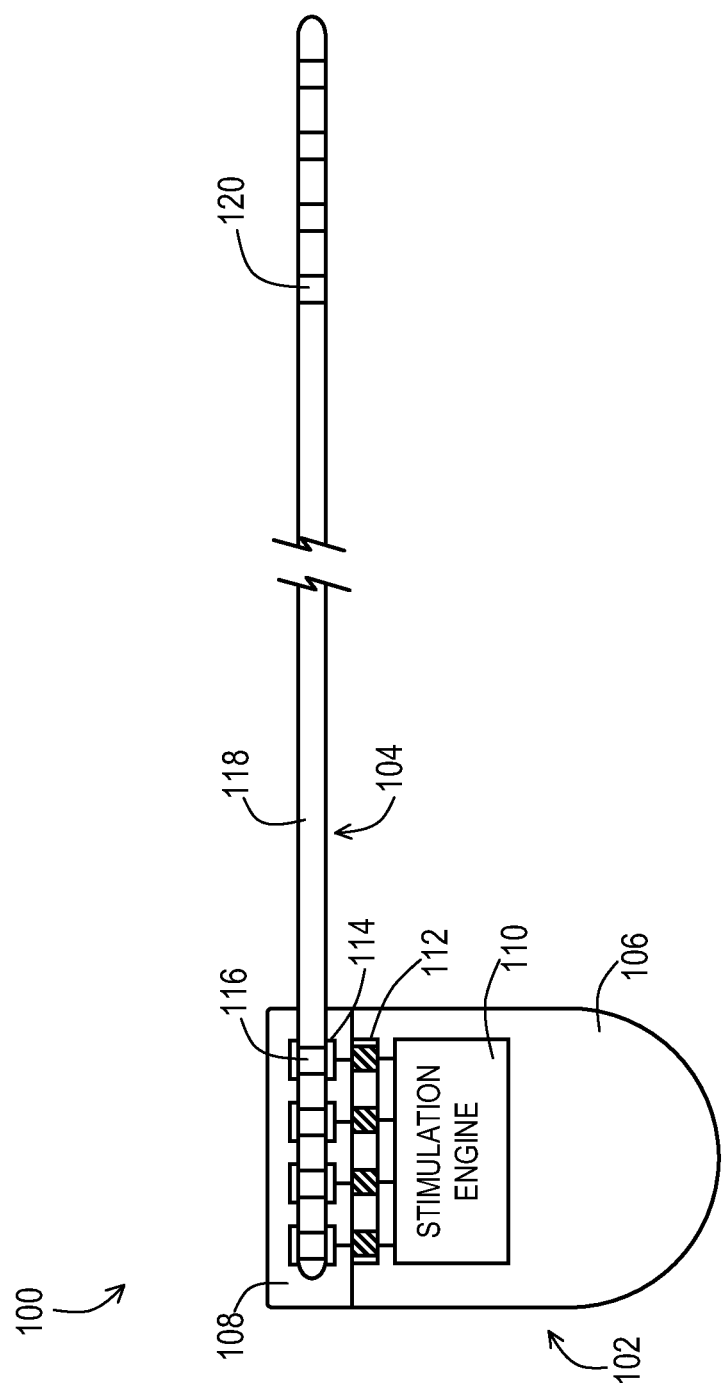
FIG. 1 shows an example of an implantable medical system that may include embodiments of the lead to reduce the coupling of the shield to the lead conductor(s).

FIG. 1 shows an example of an implantable medical system 100 that may be used to provide electrical stimulation therapy and that may reduce coupling between a shield and a conductor of a lead 104. The implantable medical system 100 includes a pulse generator 102 that includes a housing 106 that contains a stimulation engine 110 that produces the electrical stimulation signals. The pulse generator 102 may include a header 108 that includes a bore that receives a proximal end of the lead 104. The header 108 includes electrical connectors 114 that physically contact conductive contacts 116 of the lead 104. A feedthrough 114 transfers electrical signals from the sealed housing 106 to the connectors 114 of the header 104.

Figure 2A:
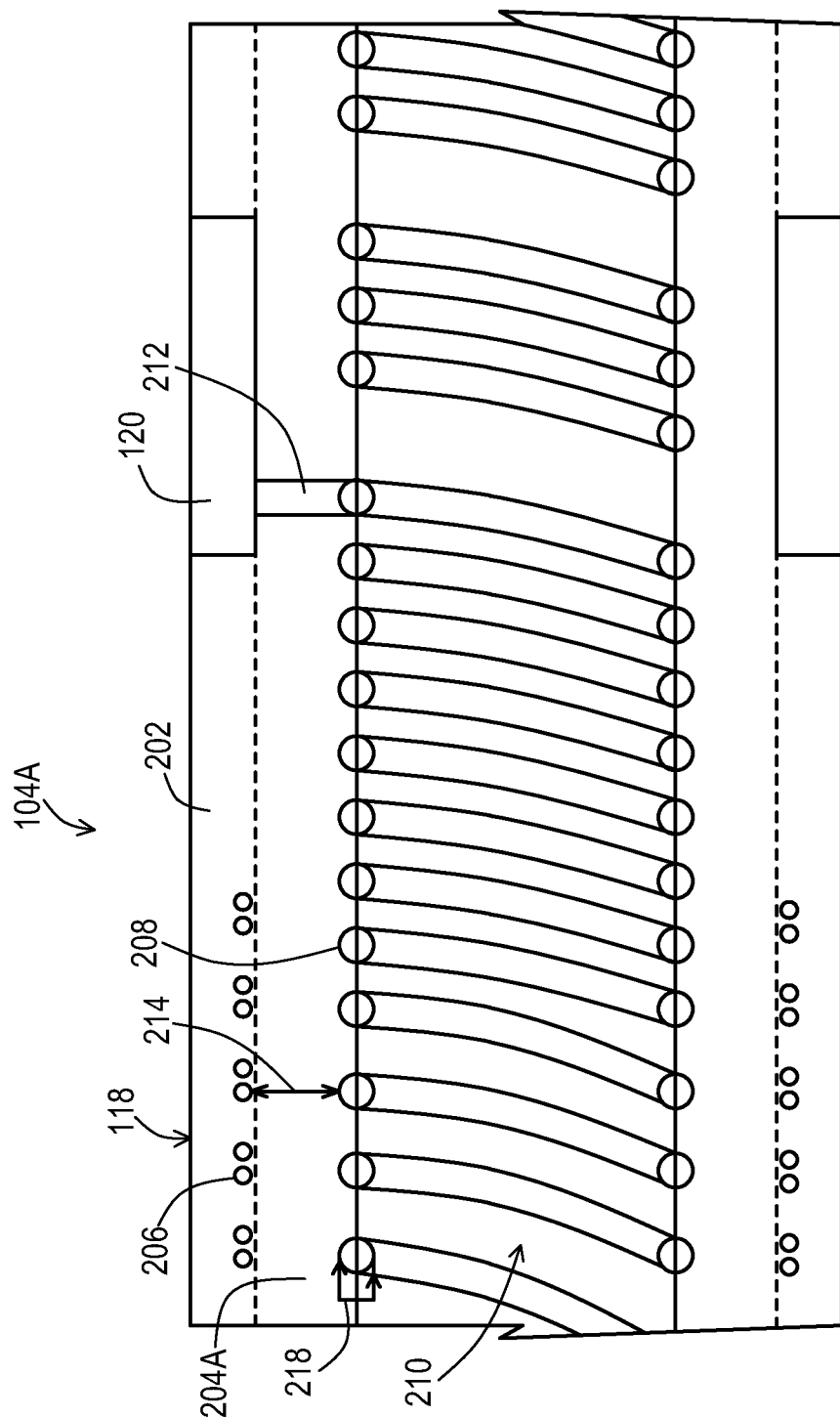
FIG. 2A shows a first example of a longitudinal cross-section of an implantable medical lead that includes a full-length partially embedded conductor to reduce the coupling of the shield to the lead conductor(s).

The lead 104 carries the electrical signals from the contacts 114 to the electrodes 120 that are coupled to the distal end of the lead body and are located at the target site within the body. FIG. 2A shows a longitudinal cross-section of a first example of the lead 104A. In this example, the lead 104A includes a collection of coiled conductors 208 that are electrically coupled to the contacts 114 of FIG. 1 and to the electrodes 120 via a radially extending portion 212. The lead 104A also includes a radio frequency (RF) shield 206 that in this example is a braid of conductive wires where the braid surrounds the conductors 208. In this example, the shield 20 is encapsulated within the lead body 118 where the lead body 118 is constructed within an insulative inner layer 204A and an insulative outer layer 202 overmolded onto the shield 206 and the inner layer 204A. Each of these layers 202, 204A may be various biocompatible and mechanically compliant materials such as polyurethane or silicone rubber. These layers 202, 204A and may have varying degrees of hardness ranging, for instance according to some embodiments the hardness may range from Shore 45 A to Shore 80 D.

As can be seen in this cross-section, the conductor 208 has a diameter 218 and the conductor 208 is partially embedded with a portion of the diameter 218 residing within the inner layer 204A and a portion residing within a lumen 210. In this example, one half of the diameter is embedded but it will be appreciated that the amount of the diameter 218 that is embedded may vary from one application to another. The conductor 208 in this example is partially embedded over the entire length of the conductor 208 from the proximal end at the contact 114 to the distal end at the electrode 114, which provides a high degree of isolation of the conductors 208 from the shield 206. A space 214 exists between the shield 206 and the conductors 208, and the inner layer 204A entirely fills the space 214 such that body fluids cannot pool between the conductors 208 and the shield 206. The coupling of the shield 206 to the conductor 208 is inhibited to avoid unwanted currents being channeled from the shield 206 to the conductors 208.

Figure 2B:
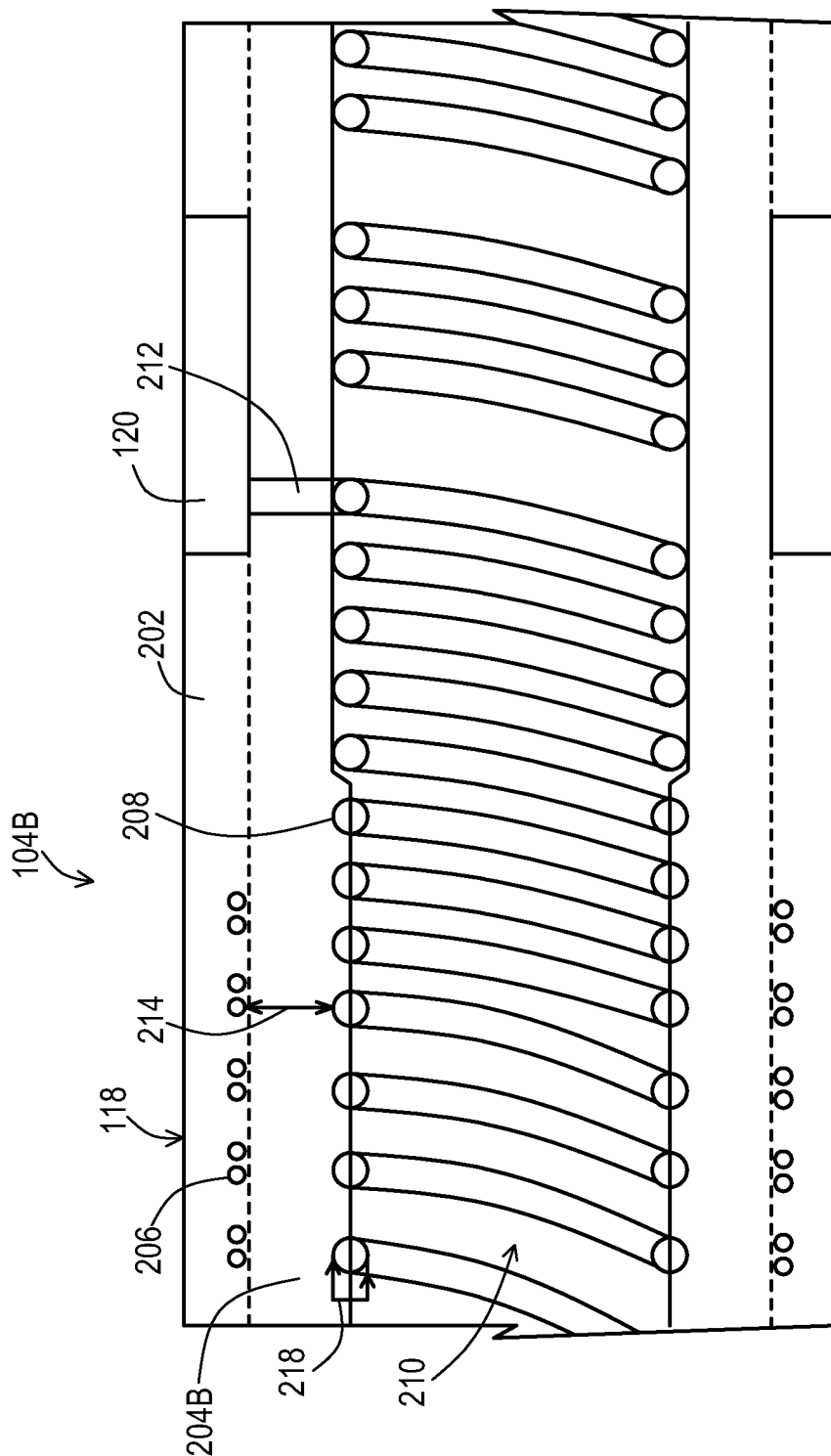
FIG. 2B shows a second example of a longitudinal cross-section of an implantable medical lead that includes a partial-length partially embedded conductor to reduce the coupling of the shield to the lead conductor(s).

FIG. 2B shows another example of a lead 104B. In this example, a first longitudinal section of the conductor 208 is partially embedded into the inner layer 204B of the lead body 118, such as one half of the diameter 218 being embedded as shown. However, the conductors 208 are not embedded to this degree over the full length and become less embedded, including being completely unembedded as shown, at a second longitudinal section in an area between a termination of the shield 206 and the proximal edge of the distal electrode 120. The conductor 208 may be less embedded by the inside diameter of the inner layer 204 increasing in size as shown, or by the outer diameter of the coil of the conductor 208 shrinking in size. This configuration continues to isolate the conductors 208 from the shield 206 to a high degree as the conductor 208 remains embedded in layer 204B for some distance beyond the shield termination but provides greater mechanical compliance of the conductors 208 near the electrodes 120 which may be beneficial in some situations.

Figure 2C:
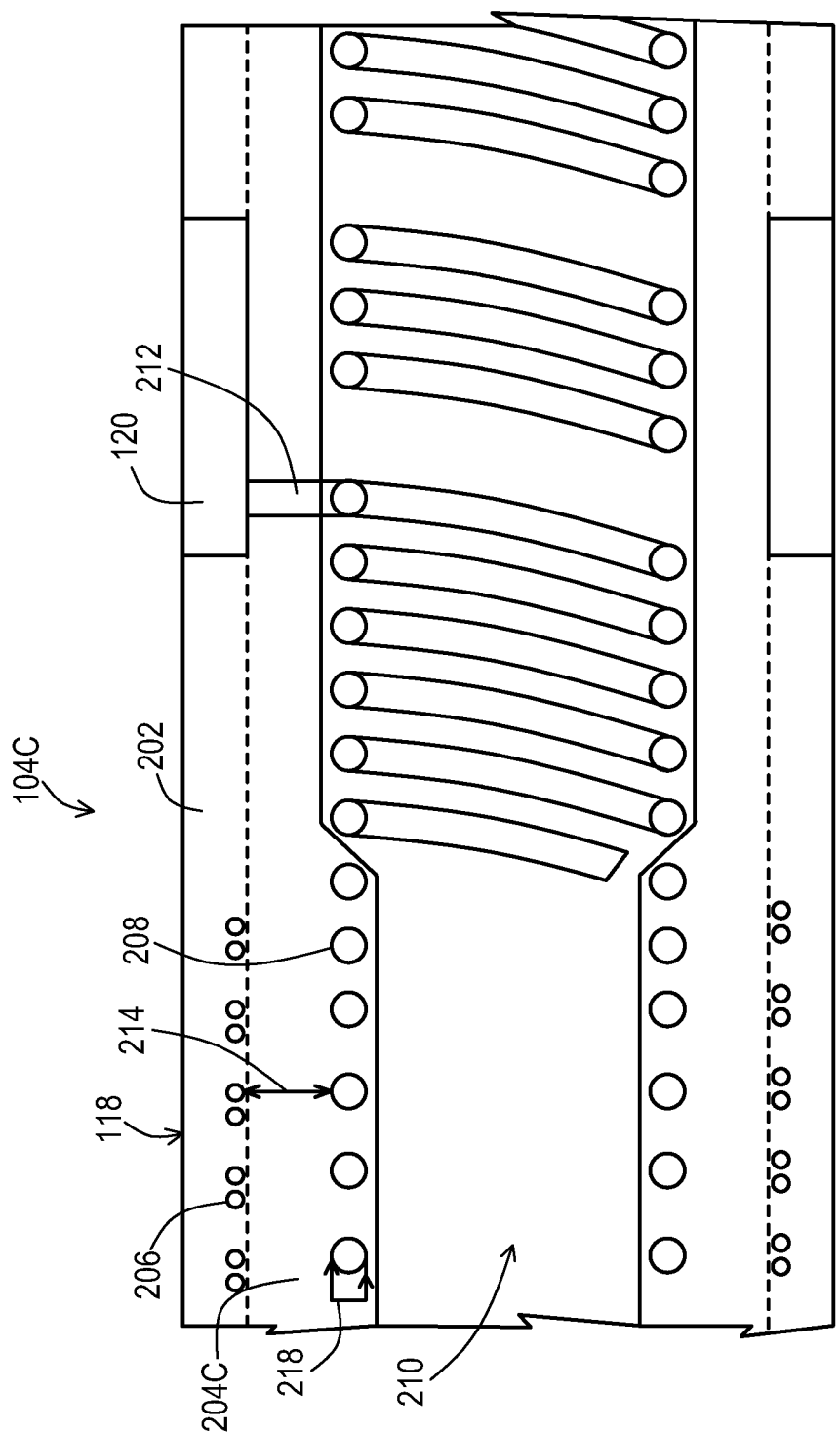
FIG. 2C shows a third example of a longitudinal cross-section of an implantable medical lead that includes a partial-length fully embedded conductor to reduce the coupling of the shield to the lead conductor(s).

FIG. 2C shows another example of a lead 104C. In this example, a first longitudinal section of the conductor 208 is fully embedded into the inner layer 204C of the lead body 118 with the full diameter 218 being present within the inner layer 204C. However, the conductors 208 are not embedded to this degree over the full length and become less embedded, including being completely unembedded as shown, at a second longitudinal section in an area between a termination of the shield 206 and the proximal edge of the distal electrode 120. This configuration continues to isolate the conductors 208 from the shield 206 to a high degree while providing increased stiffness relative to a partially embedded state as in FIG. 2B. However, like the example in FIG. 2B, the lesser embedded portion provides greater mechanical compliance of the conductors 208 near the electrodes 120 which may be beneficial in some situations.

Figure 2D:
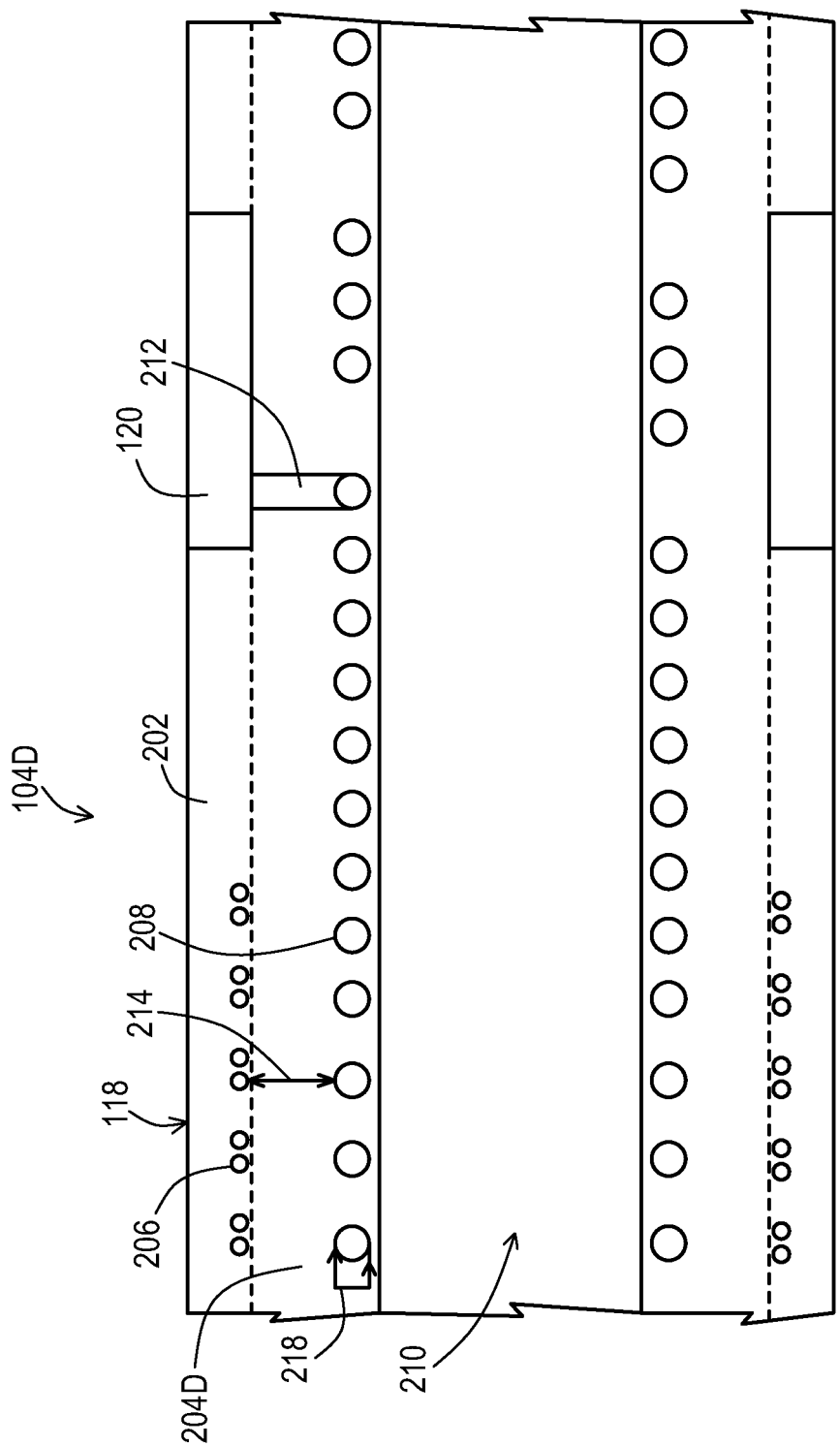
FIG. 2D shows a fourth example of a longitudinal cross-section of an implantable medical lead that includes a full-length fully embedded conductor to reduce the coupling of the shield to the lead conductor(s).

FIG. 2D shows another example of a lead 104D. In this example, the conductor 208 is fully embedded into the inner layer 204C of the lead body 118 with the full diameter 218 being present within the inner layer 204C. In this case, the conductors 208 are fully embedded over the full length from the contact 114 to the electrode 120. This configuration continues to isolate the conductors 208 from the shield 206 to a high degree while providing increased stiffness relative to a partially embedded state as in FIG. 2C and additionally stiffness at the electrodes 214 as well, which may be beneficial in some situations.

Figure 2E:
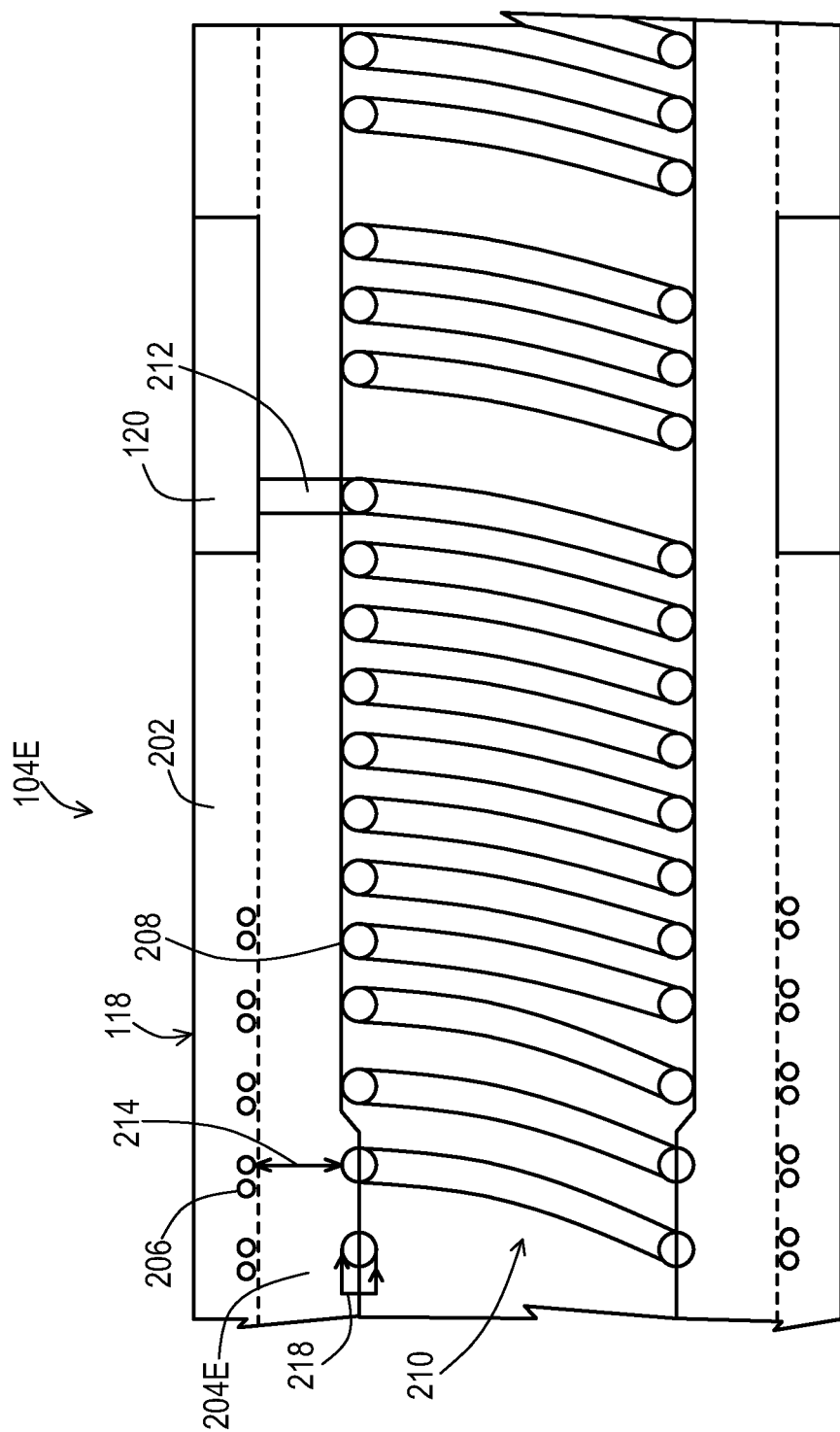
FIG. 2E shows a fifth example of a longitudinal cross-section of an implantable medical lead that includes a partial-length embedded conductor to reduce the coupling of the shield to the lead conductor(s) while providing increased conductor compliance near the electrode.

FIG. 2E shows another example of a lead 104E. In this example, a first longitudinal section of the conductor 208 is partially embedded into the inner layer 204E of the lead body 118, such as one half of the diameter 218 being embedded as shown or could also be fully embedded. However, the conductors 208 are not embedded to this degree over the full length and become less embedded, including being completely unembedded as shown, at a second longitudinal section prior to a termination of the shield 206. This configuration continues to isolate the conductors 208 from the shield 206 over a significant length of the conductor 208 but provides significantly greater mechanical compliance of the conductors 208 near the electrodes 120 where this larger degree of mechanical compliance near the electrodes 120 may be beneficial in some situations.

Figure 3:
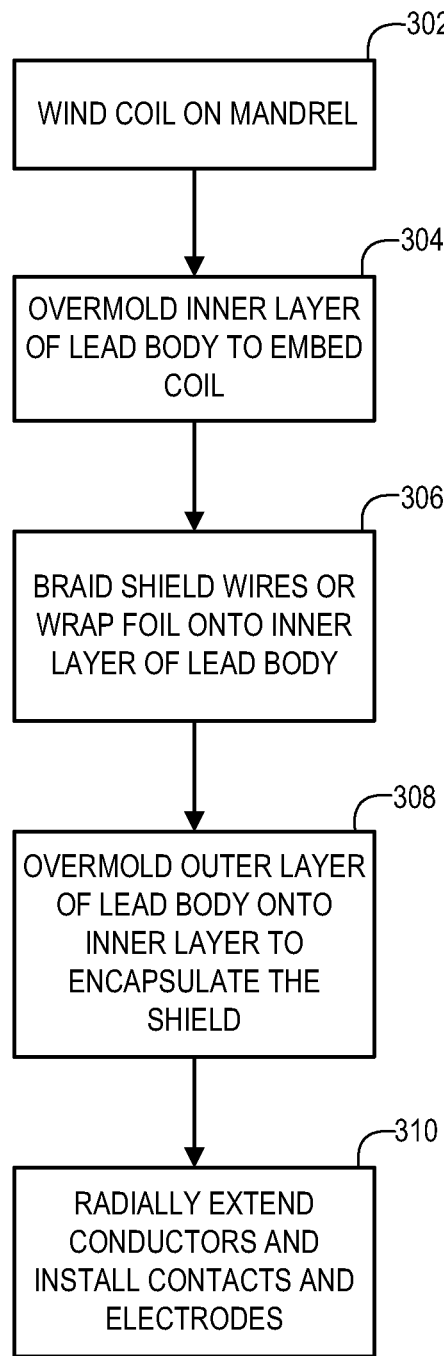
FIG. 3 shows an example of a set of operations to construct an implantable medical lead with a conductor that is at least partially embedded according to the embodiments of FIGS. 2A-2D.

FIG. 3 shows one example of a set of operations used to construct the embodiments of the lead 104. In this example, the conductors 208 are coiled and therefore straight wires are coiled around a mandrel at a coiling operation 302 to form the coiled conductors 208. The conductors may be coiled at the desired pitch and spacing as is typical for coiled conductors in medical leads. An inner layer 204 of the insulative lead body 118 is then overmolded onto the coiled conductors 208 at a molding operation 304. The overmolding may occur while the coiled conductors 208 remain on the coiling mandrel or the coiled conductors 208 may first be removed from the coiling mandrel and placed on a molding mandrel such as a stainless steel pin or wire that is coated with a polytetrafluoroethylene (PTFE) such as the Teflon® polymer from the DuPont Corporation. This overmolding operation 304 dictates the degree to which the diameter 214 of the conductors 208 is embedded into the inner layer 204. This overmolding operation 304 also dictates the length of the conductors 208 that become embedded. The overmolding operation 304 may be performed by using a heat shrink tubing as at least a portion of the inner layer 204 that contacts the conductors 208. The depth to which the diameter of the conductors 208 is present within the heat shrink tubing is controlled by the amount of shrink resulting from the chosen time and temperature of the heat shrink process. In that case, the longitudinal length of the conductors 208 that are at least partially embedded into the layer 204 is controlled by the length of the heat shrink tubing being applied to the conductors 208.

At this point, the lead assembly is ready for application of the shield 206, which may be created by braiding wires onto the inner layer 204 of the lead body 118 at a shielding operation 306. As an alternative, a conductive foil may be wrapped around the inner layer 204 at the shielding operation 306 to provide the shielding. The outer layer 202 of the lead body 118 is then overmolded atop the shielding 206 at a molding operation 308 in order to encapsulate the shield within the lead body 118. The construction of the lead 104 is completed at a conductor operation 310 by radially extending the conductor portion 212 to the position for the contact 116 on the proximal end and to the position for the electrode 120 on the distal end. The contact 116 and the electrode 120 are installed onto their respective positions on the lead body 118 with a weld or other conductive bond of the conductors 208 to the corresponding contacts 116 and electrodes 120. Other methods of manufacture may also be done, such as extruding the polymer layer over the coil while present on the mandrel, although the starting and stopping points along the length of the coil where the coil is being embedded may be less precise than where a heat shrink with a specified length is being used to achieve the embedding.

As discussed above, cabled conductors may be used in place of coiled conductors and in such a case, the cabled conductors may be positioned at their designated circumferential positions on a molding pin. Then the cabled conductors are overmolded with the inner layer 204 at the molding operation 304 and the process of FIG. 3 continues.

While embodiments have been particularly shown and described, it will be understood by those skilled in the art that various other changes in the form and details may be made therein without departing from the spirit and scope of the invention.

What is claimed is:

1. A method of providing a medical lead, comprising: providing a conductor having a diameter;
providing a lead body with a lumen, the lead body surrounding the conductor with a portion of the conductor diameter being embedded within the lead body such that a first portion of the conductor diameter is present within the lumen and a second portion of the conductor diameter is sunken into a lumen wall forming the lumen; and
providing an electrode attached to the lead body and electrically coupled to the conductor.

2. The method of claim 1, further comprising providing a radio frequency (RF) shield that surrounds the conductor such that a space exists between the shield and the conductor, wherein the lead body encapsulates the shield and the lead body fills the space.

3. The method of claim 2, wherein the shield comprises wires.

4. The method of claim 2, wherein the shield terminates prior to the location of the electrode and the portion of the diameter of the conductor is embedded within the lead body in an area of the lead body between the termination of the shield and the electrode.

5. The method of claim 1, wherein the conductor is coiled.

6. The method of claim 1, wherein half of the diameter of the conductor is embedded within the lead body and half of the diameter of the conductor is present within the lumen.

7. A method of providing a medical lead, comprising:
forming an inner lead body layer of a lead body about a conductor to embed a first lengthwise portion of the conductor within the inner lead body layer such that the first lengthwise portion of the conductor is at least partially sunken into a lumen wall forming a lumen in the inner lead body layer while a second lengthwise portion of the conductor resides in the lumen and is surrounded by the lumen wall;
forming an outer lead body layer of the lead body about the inner lead body layer to bond with the inner lead body layer; and
providing an electrode attached to the lead body and electrically coupled to the conductor.

8. The method of claim 7, further comprising positioning a metal radio frequency (RF) shield about the lead body inner layer and wherein the outer lead body encapsulates the shield.

9. The method of claim 8, wherein the shield comprises wires.

10. The method of claim 9, wherein the shield comprises braided wires.

11. The method of claim 8, wherein the shield terminates prior to the location of the electrode and the first lengthwise portion of the conductor is embedded within the inner lead body layer in an area of the lead body between the termination of the shield and the electrode.

12. The method of claim 7, wherein the conductor is coiled.

13. An implantable medical lead,
comprising: a conductor having a diameter;
a lead body with a lumen, the lead body surrounding the conductor with a portion of the conductor diameter being embedded within the lead body such that a first portion of the conductor diameter is present within the lumen and a second portion of the conductor diameter is sunken into a lumen wall forming the lumen; and
an electrode attached to the lead body and electrically coupled to the conductor.

14. The implantable medical lead of claim 13, further comprising a radio frequency (RF) shield that surrounds the conductor such that a space exists between the shield and the conductor, wherein the shield is encapsulated within the lead body and the lead body fills the space.

15. The lead of claim 14, wherein the shield comprises wires.

16. The lead of claim 14, wherein the shield terminates prior to the location of the electrode and the portion of the diameter of the conductor is embedded within the lead body in an area of the lead body between the termination of the shield and the electrode.

17. The lead of claim 13, wherein the conductor is coiled.

18. The lead of claim 13, wherein half of the diameter of the conductor is embedded within the lead body and half of the diameter of the conductor is present within the lumen.

19. An implantable medical system,
comprising: a pulse generator; and
a medical lead, comprising:
a conductor having a diameter, the conductor being electrically coupled to the pulse generator;
a lead body with a lumen, the lead body surrounding the conductor with a portion of the conductor diameter being embedded within the lead body such that a first portion of the conductor diameter is present within the lumen and a second portion of the conductor diameter is sunken into a lumen wall forming the lumen; and
an electrode attached to the lead body and electrically coupled to the conductor.

20. The implantable medical system of claim 19, further comprising a radio frequency (RF) shield that surrounds the conductor such that a space exists between the shield and the conductor, wherein the lead body encapsulates the shield and the lead body fills the space.

21. The system of claim 20, wherein the shield comprises wires.

22. The system of claim 20, wherein the shield terminates prior to the location of the electrode and the portion of the diameter of the conductor is embedded within the lead body in an area of the lead body between the termination of the shield and the electrode.

23. The system of claim 19, wherein the conductor is coiled.

24. The system of claim 19, wherein half of the diameter of the conductor is embedded within the lead body and half of the diameter of the conductor is present within the lumen.

25. An implantable medical lead, comprising: a conductor having a diameter;
a lead body with a lumen, the lead body surrounding the conductor with a first longitudinal section of the conductor diameter being at least partially embedded within the lead body such that the conductor is at least partially sunken into a lumen wall forming the lumen and with a second longitudinal section of the conductor diameter that is distal of the first longitudinal section and being less embedded by the lead body than the first section; and
an electrode attached to the lead body and electrically coupled to the conductor.

26. The implantable medical lead of claim 25, comprising a radio frequency (RF) shield that surrounds the conductor such that a space exists between the shield and the conductor, wherein the lead body encapsulates the shield and the lead body fills the space between the first section of the conductor and the shield.

* * * * *